（12） United States Patent
Nakata

(10) Patent No.: US 8,454,530 B2
(45) Date of Patent: Jun. 4, 2013

(54) BIOPSY APPARATUS AND BIOPSY METHOD

(75) Inventor: Hajime Nakata, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 340 days.

(21) Appl. No.: 12/751,472

(22) Filed: Mar. 31, 2010

(65) Prior Publication Data

US 2010/0249648 A1    Sep. 30, 2010

(30) Foreign Application Priority Data

Mar. 31, 2009    (JP) .................................. 2009-085879

(51) Int. Cl.
*A61B 5/00*    (2006.01)
(52) U.S. Cl.
USPC ........................................................ 600/564
(58) Field of Classification Search
USPC .................................................. 600/564–568
See application file for complete search history.

(56) References Cited

U.S. PATENT DOCUMENTS

| | | | |
|---|---|---|---|
| 5,584,292 A | 12/1996 | Cheung | |
| 5,594,769 A * | 1/1997 | Pellegrino et al. | 378/37 |
| 5,964,715 A * | 10/1999 | Thunberg | 600/562 |
| 6,592,257 B1 | 7/2003 | Heidsieck et al. | |
| 2004/0171933 A1 | 9/2004 | Stoller et al. | |
| 2007/0263765 A1 * | 11/2007 | Wu | 378/37 |

FOREIGN PATENT DOCUMENTS

| | | |
|---|---|---|
| JP | 10-201749 A | 8/1998 |
| JP | 2001-504002 A | 3/2001 |
| JP | 2002-186623 A | 7/2002 |
| JP | 2004-081330 A | 3/2004 |
| JP | 2005013311 A | 1/2005 |
| JP | 3668741 B2 | 4/2005 |
| JP | 2007229201 A | 9/2007 |
| WO | 2006/030406 A2 | 3/2006 |
| WO | 2006/030406 A3 | 3/2006 |
| WO | 2006/030436 A2 | 3/2006 |
| WO | 2007095330 A2 | 8/2007 |

OTHER PUBLICATIONS

European Search Report dated Jun. 11, 2010, corresponding to Application No. 10157614.81265.
Notification of First Office Action, dated Aug. 2, 2012, issued in corresponding CN Application No. 201010156951, 19 pages in English and Chinese.
Rejection of the Application, dated Dec. 11, 2012, issued in corresponding JP Application No. 2009-085879, 6 pages in English and Japanese.

* cited by examiner

*Primary Examiner* — Max Hindenburg
(74) *Attorney, Agent, or Firm* — Sughrue Mion, PLLC

(57) ABSTRACT

A biopsy apparatus has a biopsy needle, which faces a radiation reception surface of a radiation detector and is held obliquely to the radiation reception surface by a biopsy needle holding mechanism. The biopsy apparatus includes a radiographic image capturing apparatus for capturing two radiographic images. One of the two radiographic images is produced according to a scout image capturing mode or a stereographic image capturing mode, and the other is produced according to the stereographic image capturing mode.

13 Claims, 12 Drawing Sheets

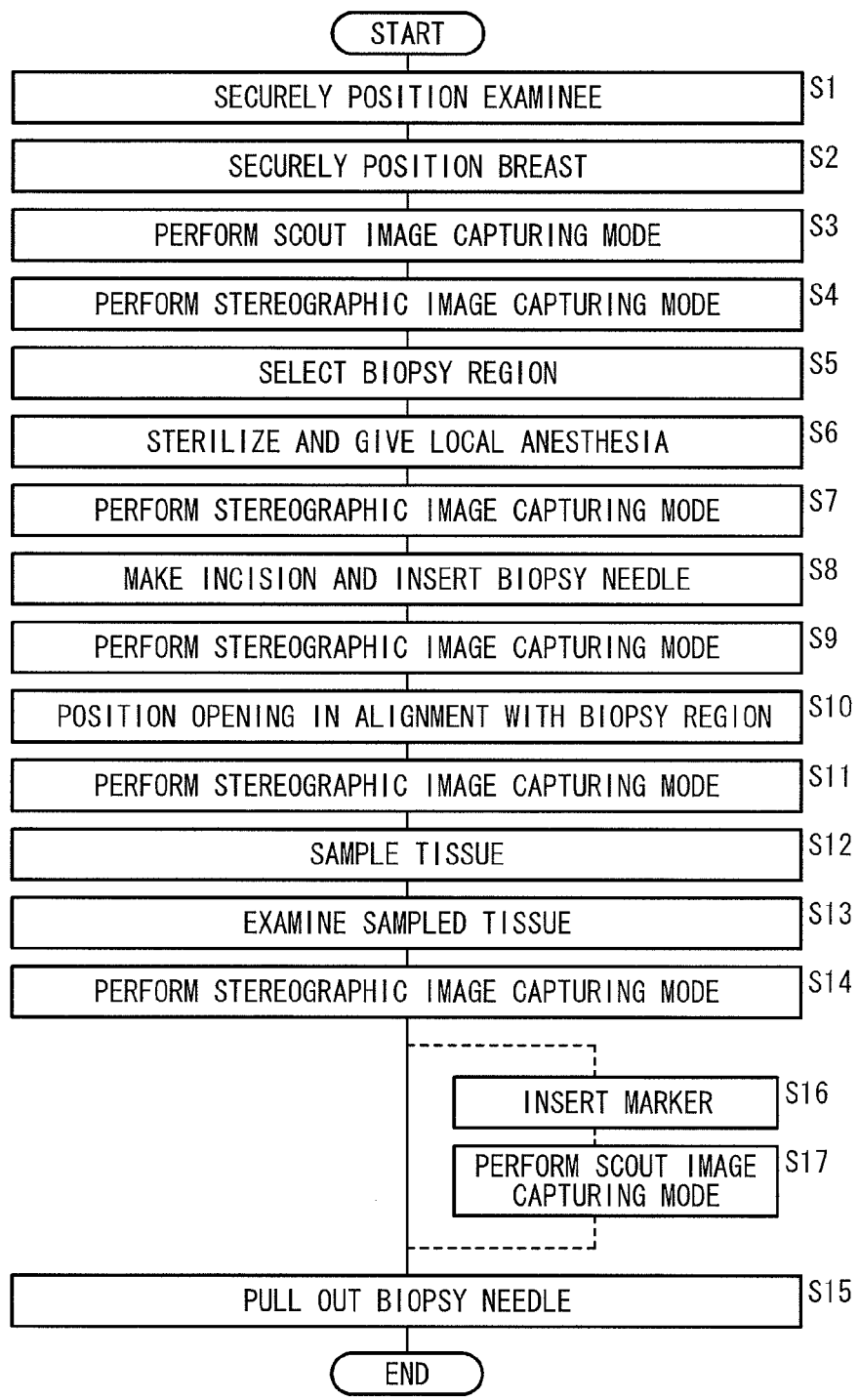

BIOPSY APPARATUS AND BIOPSY METHOD

CROSS-REFERENCE TO RELATED APPLICATION

This application is based upon and claims the benefit of priority from Patent Application No. 2009-085879 filed on Mar. 31, 2009, in the Japan Patent Office, of which the contents are incorporated herein by reference.

BACKGROUND OF THE INVENTION

1. Field of the Invention

The present invention relates to a biopsy apparatus and a biopsy method for calculating a three-dimensional position of a region to be biopsied (hereinafter referred to as a "biopsy region") of an object to be examined, based on at least two radiographic images obtained by irradiating the object with radiation from directions that are different from each other, then moving a biopsy needle to the biopsy region based on the calculated three-dimensional position, and removing a tissue sample from the biopsy region.

2. Description of the Related Art

Heretofore, biopsy apparatus have been developed in the art for removing a tissue sample from a biopsy region of an object to be examined (e.g., an inflicted region of a breast of a subject) and examining the tissue sample to perform a disease diagnosis of the subject. In order to identify the position of the biopsy region, the biopsy apparatus incorporates a radiographic image capturing apparatus, which captures a plurality of radiographic images under a stereographic image capturing mode by applying radiation to the object from directions that are different from each other. The three-dimensional position of the biopsy region is specified using the captured radiographic images. Then, a biopsy needle is moved toward the biopsy region based on the specified three-dimensional position, and a tissue sample is removed from the biopsy region.

Techniques for specifying the position of a biopsy region using a plurality of radiographic images, techniques for removing a tissue sample from the biopsy region, and techniques concerning radiographic image capturing apparatus incorporated in biopsy apparatus have been proposed or disclosed in Japanese Patent No. 3668741, Japanese Laid-Open Patent Publication No. 2001-504002 (PCT), Japanese Laid-Open Patent Publication No. 10-201749, and Japanese Laid-Open Patent Publication No. 2002-186623.

It is proposed in Japanese Patent No. 3668741 that a scintillator of a radiation detector converts radiation into light, and that a CCD array converts the light into a radiation image.

It is proposed in Japanese Laid-Open Patent Publication No. 2001-504002 (PCT) that the cassette of a radiation detector is separated from a radiographic image capturing apparatus when the cassette is not in use.

It is proposed in Japanese Laid-Open Patent Publication No. 10-201749 to acquire two radiographic images by irradiating a phantom having a marker, which is disposed in a known position, with radiation at two angles, whereby a calculating algorithm for identifying the position of a biopsy region is modified based on the acquired two radiographic images and the position of the marker of the phantom.

Japanese Laid-Open Patent Publication No. 2002-186623 discloses that a biopsy needle is inserted obliquely into a biopsy region in order to remove sample tissue therefrom.

In a stereographic image capturing mode that applies radiation to an object from different directions, since plural radiographic images need to be captured in order to identify the position of the biopsy region, the dose of radiation applied to the examinee is increased. Further, the time required to examine the biopsy region depends on the skill of the doctor or technician who uses the biopsy apparatus. Therefore, if the doctor or technician who uses the biopsy apparatus is not skilled, then the examination process becomes time-consuming, and tends to hold the object for a long period of time. Consequently, it would be desirable to reduce the number of radiographic images that are captured, for thereby minimizing the dose of applied radiation and shortening the time required for the examination process.

According to Japanese Patent No. 3668741, since a CCD array is used to capture a radiographic image of an object, the object is exposed to radiation at all times, and hence the applied radiation dose is high. According to Japanese Laid-Open Patent Publication No. 2001-504002 (PCT), since eight to ten radiographic images need to be captured in order to identify the position of the biopsy region, the number of captured radiographic images cannot be reduced, and further, the applied radiation dose cannot be reduced. Japanese Laid-Open Patent Publication No. 10-201749 and Japanese Laid-Open Patent Publication No. 2002-186623 do not propose any techniques or methods aimed at reducing the number of radiographic images required to be captured so as to reduce the applied radiation dose. In addition, attempts to shorten the time required for the examination process by reducing the number of captured radiographic images have not been proposed in Japanese Patent No. 3668741, Japanese Laid-Open Patent Publication No. 2001-504002 (PCT), Japanese Laid-Open Patent Publication No. 10-201749, or Japanese Laid-Open Patent Publication No. 2002-186623.

Japanese Laid-Open Patent Publication No. 2001-504002 (PCT) discloses that the angle of a radiation source with respect to the perpendicular axis of a radiation reception surface of the radiation detector is set to ±15° in a stereographic image capturing mode. The angle of the radiation source is set this way because if a scout image capturing mode is performed to irradiate the object with radiation emitted from a radiation source disposed on the perpendicular axis (0°), then the biopsy needle also is imaged in overlapping relation to the biopsy region in the radiographic image captured in the scout image capturing mode, thus making it impossible to identify the position of the biopsy region. According to Japanese Laid-Open Patent Publication No. 2001-504002 (PCT), in order to prevent the biopsy needle from being imaged, the biopsy region is imaged while capturing two radiation images, i.e., when the radiation source is positioned at an angle of +15° and an angle of −15° respectively, whereby the position of the biopsy region is identified using the two captured radiographic images.

In the scout image capturing mode, scattered rays of radiation, which are generated when radiation is applied to the object, are removed by a grid. The grid is of a structure having an alternate pattern made up of one material, which is permeable to radiation, and another material, which absorbs radiation. The grid is disposed near the radiation reception surface of the radiation detector. In the stereographic image capturing mode, since the angle of the radiation source with respect to the perpendicular axis of the radiation reception surface of the radiation detector is set to ±15°, which differs from the angle of the radiation source used in the scout image capturing mode, the radiation required to capture radiation images tends to be absorbed by the grid. Consequently, the grid cannot be used in the stereographic image capturing mode. As a result, radiation images captured in the stereographic image capturing mode may possibly be of low quality, due to such scattered radiation.

SUMMARY OF THE INVENTION

It is an object of the present invention to reduce the number of radiographic images to be captured of an object and to reduce the radiation dose applied to the object to capture radiographic images, while also shortening the time required to examine the object.

Another object of the present invention is to produce radiographic images of high quality.

To achieve the above objects, there is provided in accordance with the present invention a biopsy apparatus comprising a radiographic image capturing apparatus including a radiation source for applying radiation to an object to be examined, and a radiation detector for detecting the radiation which has passed through the object and converting the detected radiation into a radiographic image, and a biopsy needle positioning device including a biopsy region positional information calculator for calculating a three-dimensional position of a biopsy region of the object based on at least two radiographic images obtained by irradiating the object with the radiation from directions that are different from each other, a biopsy needle for piercing the biopsy region based on the calculated three-dimensional position of the biopsy region and sampling tissue of the biopsy region, and a biopsy needle holding mechanism for holding the biopsy needle, wherein the biopsy needle faces a radiation reception surface of the radiation detector and is held obliquely to the radiation reception surface by the biopsy needle holding mechanism, wherein one of the at least two radiographic images comprises either a radiographic image produced according to a scout image capturing mode, in which the object is irradiated with the radiation applied from the radiation source when the radiation source is disposed on an axis perpendicular to the radiation reception surface, or a radiographic image produced according to a stereographic image capturing mode, in which the object is irradiated with the radiation applied from the radiation source when the radiation source is disposed obliquely to the axis, and wherein the other of the at least two radiographic images comprises a radiographic image produced according to the stereographic image capturing mode.

According to the present invention, there also is provided a biopsy method comprising the steps of detecting radiation applied from a radiation source and having passed through an object to be examined, and converting the detected radiation into at least two radiation images with a radiation detector having a radiation reception surface, the two radiation images being produced either according to a scout image capturing mode, in which the object is irradiated with radiation applied from the radiation source when the radiation source is disposed on an axis perpendicular to the radiation reception surface, and a stereographic image capturing mode, in which the object is irradiated with the radiation applied from the radiation source when the radiation source is disposed obliquely to the axis, or according to the stereographic image capturing mode, calculating a three-dimensional position of a biopsy region of the object based on the at least two radiographic images with a biopsy region positional information calculator, and piercing the biopsy region with a biopsy needle based on the calculated three-dimensional position of the biopsy region and sampling tissue of the biopsy region while the biopsy needle faces the radiation reception surface and is held obliquely to the radiation reception surface by a biopsy needle holding mechanism.

Since the biopsy needle is held obliquely to the radiation reception surface of the radiation detector, the biopsy needle is reliably prevented from overlapping the biopsy region in the radiographic image produced in the scout image capturing mode. Therefore, the radiographic image produced in the scout image capturing mode can also be used as a radiographic image for identifying the three-dimensional position of the biopsy region. In other words, the three-dimensional position of the biopsy region can be identified using two radiographic images, one of which is produced in the scout image capturing mode and the other of which is produced in the stereographic image capturing mode.

For identifying the position of the biopsy region, it heretofore has been customary to perform the scout image capturing mode, confirm that the object is included in the radiographic image produced in the scout image capturing mode, thereafter move the radiation source from the imaging angle in the scout image capturing mode in order to capture a first radiographic image in the stereographic image capturing mode, then move the radiation source again from the imaging angle in the stereographic image capturing mode to another imaging angle in order to capture a second radiographic image in the stereographic image capturing mode, and subsequently identify the three-dimensional position of the biopsy region using the two radiographic images produced at respective imaging angles in the stereographic image capturing mode. Since it takes time to move the radiation source between the image capturing modes, the examination time cannot be shortened.

According to the present invention, as described above, since the radiographic image produced in the scout image capturing mode also is used as a radiographic image for identifying the three-dimensional position of the biopsy region, a second radiographic image, which heretofore has been produced in the stereographic image capturing mode, no longer is required. Rather, the three-dimensional position of the object can be identified using the radiographic image produced in the scout image capturing mode together with the first radiographic image produced in the stereographic image capturing mode. As a result, the number of captured radiographic images is reduced, and hence the dose of radiation applied to the breast also is reduced. Inasmuch as the number of captured radiographic images is reduced, the time required to move the radiation source between image capturing modes also is shortened. Therefore, the time required to examine the biopsy region can be shortened, and the object does not need to be held for a long period of time.

Furthermore, since a grid is used in the scout image capturing mode, the radiographic image produced in the scout image capturing mode is of higher quality than the radiographic image produced in the stereographic image capturing mode. Accordingly, a radiographic image of high quality can be used to identify the three-dimensional position of the biopsy region. In other words, the three-dimensional position of the biopsy region can be identified with high accuracy using both the radiographic image of high quality and the first radiographic image produced in the stereographic image capturing mode.

According to the present invention, since two radiographic images can be produced in the stereographic image capturing mode, in addition to two radiographic images produced respectively in the scout image capturing mode and the stereographic image capturing mode, the present invention can easily be applied to existing biopsy apparatus.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 12 is a flowchart of an operation sequence carried out by the biopsy apparatus shown in FIG. 1.

DESCRIPTION OF THE PREFERRED EMBODIMENTS

A biopsy apparatus according to a preferred embodiment of the present invention will be described below in relation to a biopsy method with reference to the drawings.

Figure 1:
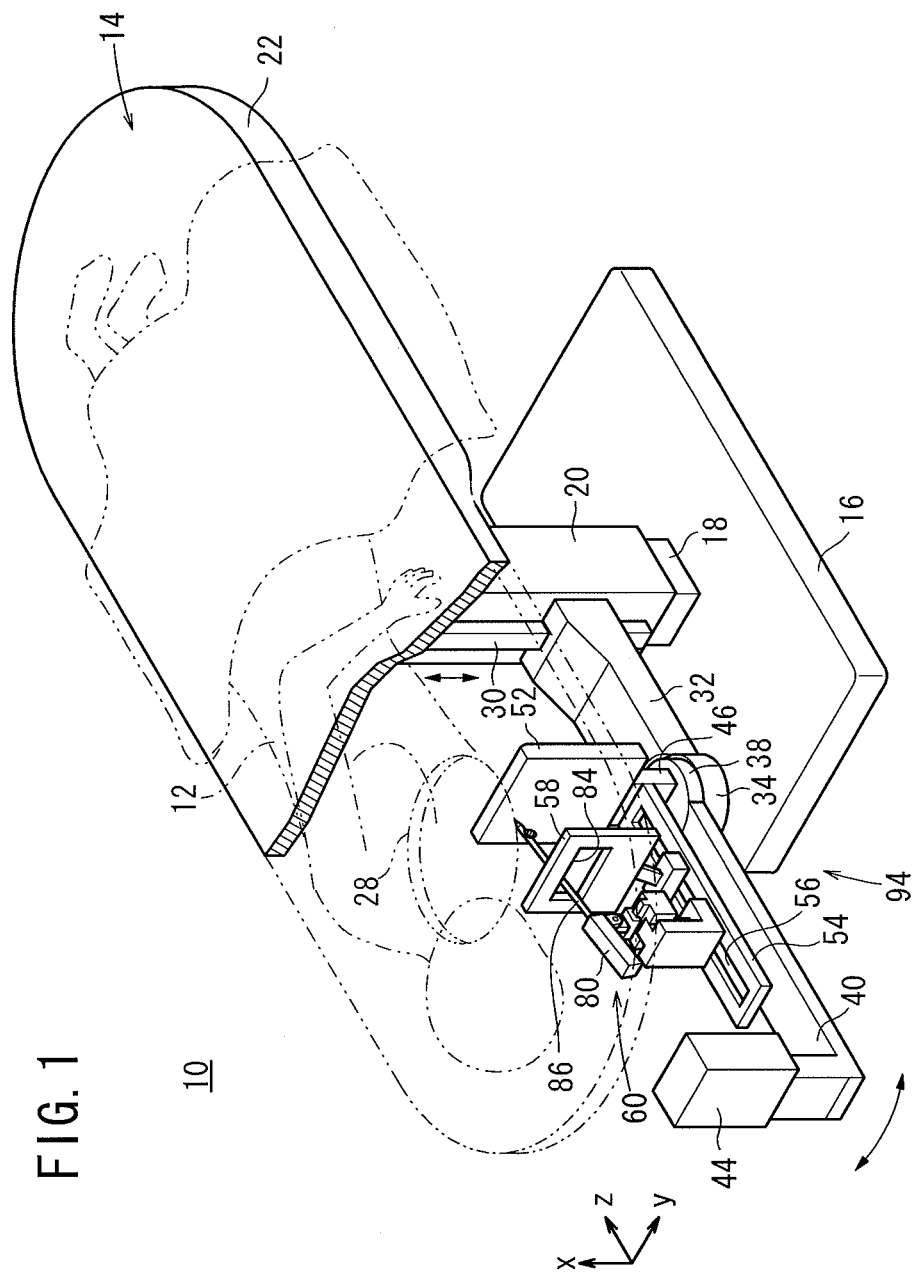
FIG. 1 is a perspective view of a biopsy apparatus according to an embodiment of the present invention.
Figure 2:
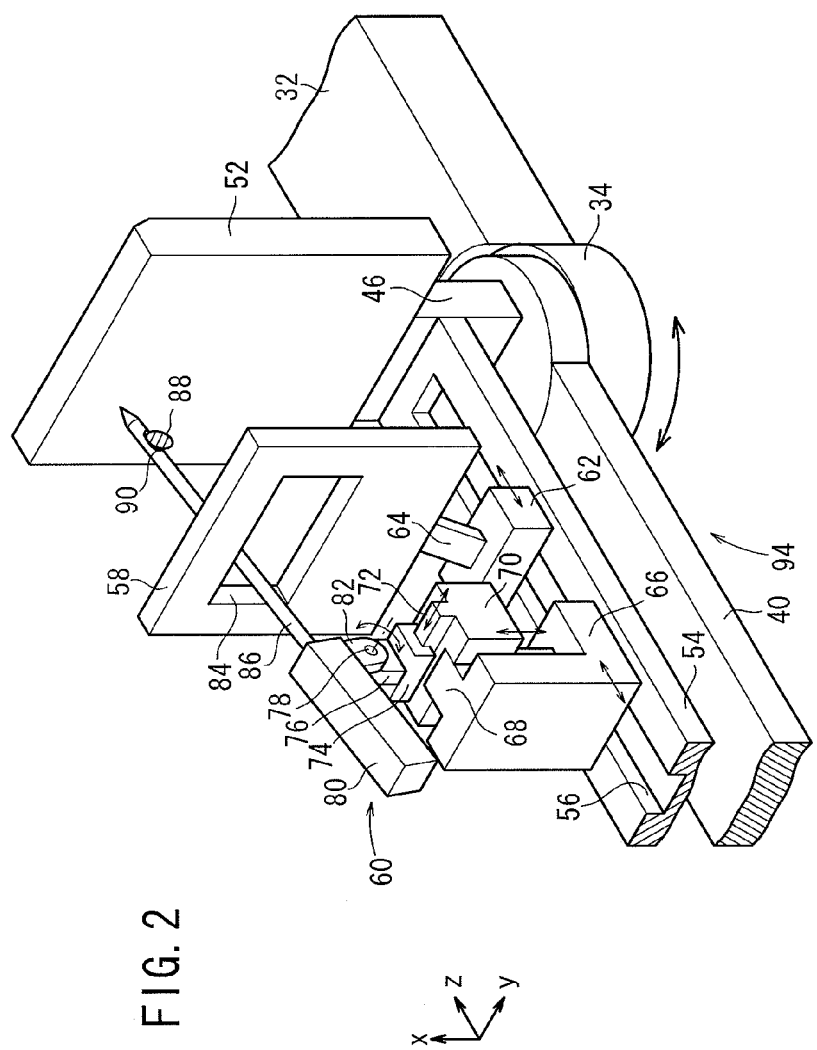
FIG. 2 is a fragmentary perspective view of the biopsy apparatus shown in FIG. 1.
Figure 3:
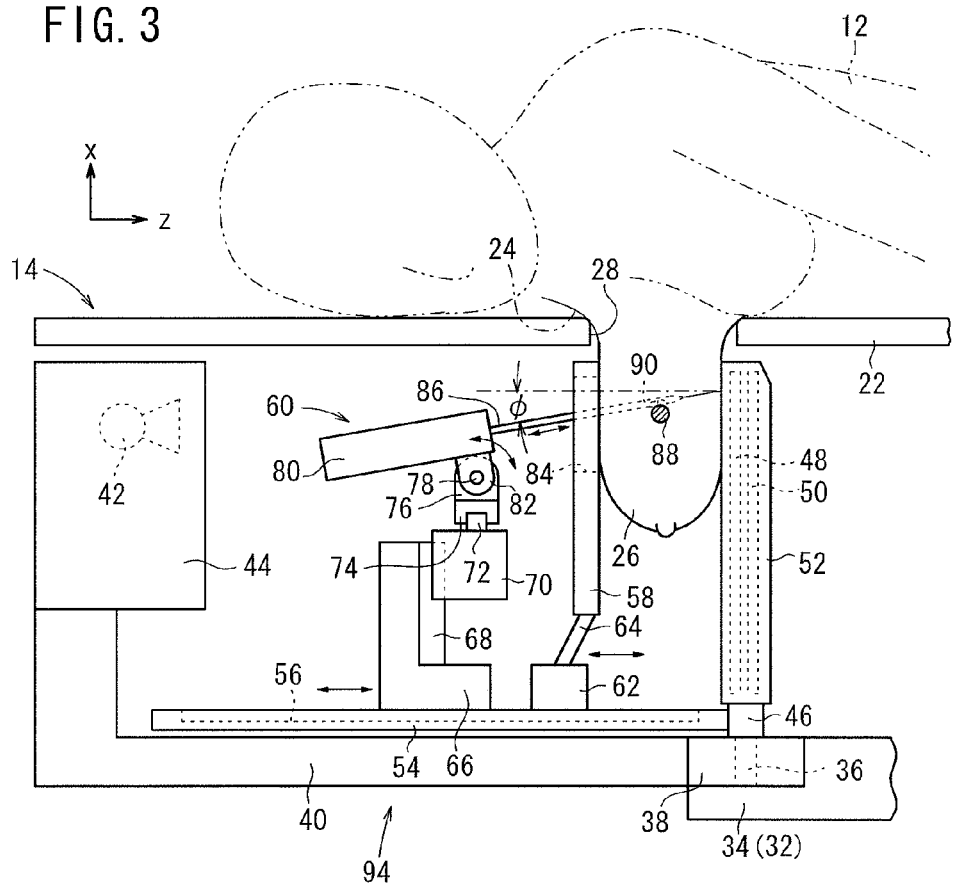
FIG. 3 is a fragmentary side elevational view of the biopsy apparatus shown in FIG. 1.

As shown in FIGS. 1 through 3, a biopsy apparatus 10 according to an embodiment of the present invention includes a bed 14 on which an examinee (subject) 12 lies. The bed 14 comprises a base 16, upstanding support members 18, 20 mounted on the base 16, and a top plate 22 supported on the support members 18, 20. The top plate 22 has an opening 28 defined therein for a breast (an object to be examined) 26 of the examinee 12. The breast hangs down through the opening when the examinee 12 lies on the top plate 22 with the chest wall 24 of the examinee 12 facing downward.

A support arm 32 is movably mounted on a side surface of the support member 20 for movement along a rail 30, which is attached to the support member 20 and extends vertically in the directions indicated by the arrow x. The support arm 32 has a distal end 34 from which a shaft 36 extends upwardly. An arm 40 has a proximal end 38 pivotally supported on the distal end 34, and a distal end to which there is fixed a radiation source casing 44 housing a radiation source 42 therein for emitting radiation 92 (see FIG. 4). The arm 40 is angularly movable about the shaft 36 in horizontal directions, within a plane that includes the directions indicated by the arrows y and z.

The shaft 36 supports on its upper distal end a support member 46, which supports thereon an image capturing base 52 housing therein a grid 48 for removing scattered rays of radiation 92 applied from the radiation source 42 to the breast 26, and a solid-state detector (radiation detector) 50 for detecting radiation 92 that has passed through the breast 26.

A guide rail 54 extends from a side surface of the support member 46 along an axis (indicated by the arrow z) perpendicular to the surface of the image capturing base 52 (the grid 48 and the solid-state detector 50). The guide rail 54 has a groove 56 defined therein, which extends along the directions indicated by the arrow z.

A support member 62, which is movable along the groove 56, is movably mounted on the guide rail 54. A compression plate 58 for compressing and holding the breast against the image capturing base 52 is mounted on the support member 62 by a support member 64.

Another support member 66, which is movable along the groove 56, is movably mounted on the guide rail 54 closer to the radiation source casing 44 than the support member 62.

The support member 66 is substantially L shaped as viewed in side elevation, and has a vertical guide rail 68 on which a slide member 70 is vertically movably supported.

The slide member 70 has a guide rail 72 disposed on the upper surface thereof, extending in the directions indicated by the arrow y. A slide member 74 is slidably mounted on the guide rail 72 for sliding movement along the guide rail 72 in the directions indicated by the arrow y. The slide member 74 has a support member 76 mounted on an upper surface thereof, and the support member 76 includes a shaft 78 extending in the directions indicated by the arrow y. A support member 82 is pivotally supported on the shaft 78, and a holster 80 including a biopsy needle 86 mounted thereon is attached to the support member 82.

The biopsy needle 86 pierces a biopsy region 88 (e.g., a calcified region) of the breast 26, which has been compressed between the compression plate 58 and the image capturing base 52, through an opening 84 defined in the compression plate 58. The biopsy needle 86 has a sampler 90 for drawing and sampling a tissue portion from the biopsy region 88.

The holster 80 serves as a manipulator for manipulating the biopsy needle 86. For example, the holster 80 causes the biopsy needle 86 to pierce the biopsy region 88, causes the sampler 90 to draw a tissue portion from the biopsy region 88, and pulls the biopsy needle 86 out from the breast 26 after the tissue portion has been sampled by the sampler 90.

The biopsy needle 86 can be displaced in directions indicated by the arrow z when the support member 66 moves along the groove 56. The biopsy needle 86 can be displaced in directions indicated by the arrow x when the slide member 70 moves along the guide rail 68. The biopsy needle 86 can be displaced in directions indicated by the arrow y when the slide member 74 moves along the guide rail 72. The biopsy needle 86 can be turned about the shaft 78 when the support member 82 and the holster 80 are turned about the shaft 78.

The support members 66, 76, 82, the guide rails 68, 72, the slide members 70, 74, the shaft 78, and the holster 80 collectively make up a biopsy needle holding mechanism 60 for holding the biopsy needle 86.

In FIG. 3, the biopsy needle 86 is inclined at an angle φ with respect to an axis (in directions indicated by the arrow z) perpendicular to the radiation reception surface (closer to the breast 26) of the solid-state detector 50. Therefore, the biopsy needle 86 obliquely pierces the biopsy region 88 for sampling a tissue portion of the biopsy region 88. The angle φ is in a range 0°<φ≦10°.

The arm 40, the radiation source casing 44 housing the radiation source 42, the support members 46, 62, 64, the image capturing base 52 housing the grid 48 and the solid-state detector 50, the guide rail 54, and the compression plate 58 collectively make up a radiographic image capturing apparatus (breast image capturing apparatus) 94.

An image capturing process performed by the radiographic image capturing apparatus 94 (biopsy apparatus 10) will be described below with reference to FIGS. 4 through 10.

The radiographic image capturing apparatus 94 performs a scout image capturing mode (see FIGS. 4 through 6), in which the breast 26 is irradiated with radiation 92 emitted from the radiation source 42, which is disposed on an axis perpendicular to the radiation reception surface of the solid-state detector 50, i.e., the directions indicated by the arrow z perpendicular to the surface of the solid-state detector 50, which is located closer to the breast 26. Alternatively, the radiographic image capturing apparatus 94 performs a stereographic image capturing mode (see FIGS. 5 through 10), in which the breast 26 is irradiated with radiation 92 emitted from the radiation source 42, which is disposed obliquely to the axis perpendicular to the radiation reception surface of the solid-state detector 50. The solid-state detector 50 detects radiation 92 that has passed through the breast 26 in the scout image capturing mode or the stereographic image capturing mode, and converts the detected radiation 92 into a radiographic image.

More specifically, the radiographic image capturing apparatus 94 captures radiographic images of the breast 26 according to either one of the image capturing processes shown in FIGS. 4 through 10.

Figure 4:
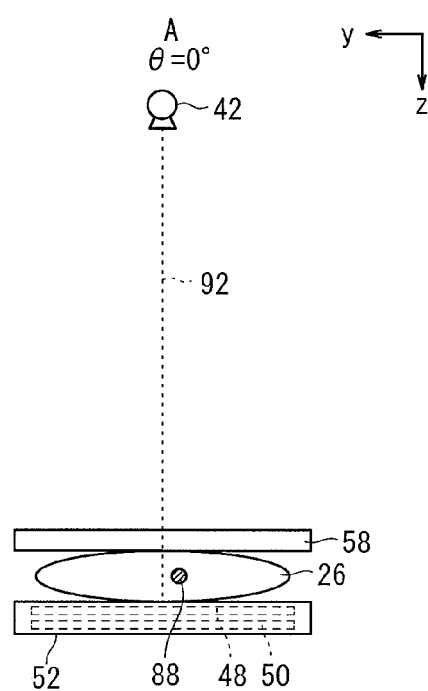
FIG. 4 is a schematic view illustrating a scout image capturing mode.

FIG. 4 shows an image capturing process for capturing a radiographic image in the scout image capturing mode. In this image capturing process, since scattered rays of radiation 92 are removed by the grid 48, the solid-state detector 50 can output a radiographic image of high quality, which is free from the effect of scattered rays. In FIG. 4, the angle $\theta$ of the radiation source 42 with respect to the radiation reception surface of the solid-state detector 50 is $\theta=0°$. The position of the radiation source 42 in the scout image capturing mode is referred to as "position A".

Figure 5:
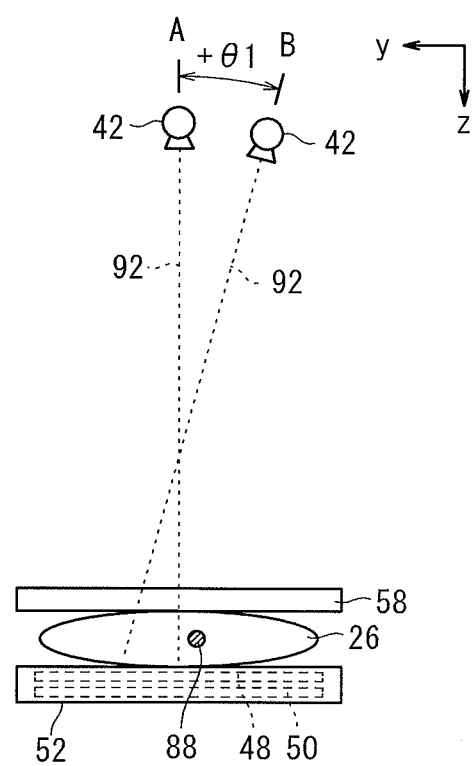
FIG. 5 is a schematic view illustrating the scout image capturing mode and a stereographic image capturing mode.

FIG. 5 shows an image capturing process for capturing a radiographic image in the scout image capturing mode together with capturing a radiographic image in the stereographic image capturing mode with the radiation source 42 placed in a position B, which is angularly spaced at an imaging angle $+\theta1$ ($+\theta1 \leq 10°$) from the position A. At the imaging angle $+\theta1$ (the position B), the radiation source 42 is not significantly inclined from the position A. Therefore, even if the grid 48 is used in the stereographic image capturing mode, the possibility that radiation 92 will be removed by the grid 48 is small. Consequently, the solid-state detector 50 can output two radiographic images of high quality, which are free from the effect of scattered rays. In FIG. 5, the scout image capturing mode and the stereographic image capturing mode may be performed in any desired order. The radiation source 42 can be moved between position A and position B by turning the arm 40 about the shaft 36.

Figure 6:
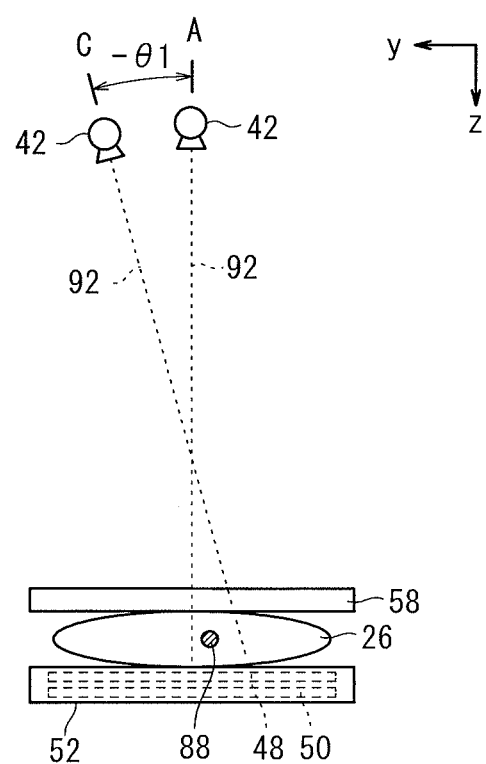
FIG. 6 is a schematic view illustrating the scout image capturing mode and the stereographic image capturing mode.

FIG. 6 shows an image capturing process for capturing a radiographic image in the scout image capturing mode together with capturing a radiographic image in the stereographic image capturing mode with the radiation source 42 placed in a position C, which is angularly spaced at an imaging angle $-\theta1$ ($|-\theta1| \leq 10°$) from the position A. At the imaging angle $-\theta1$ (the position C), the radiation source 42 is not significantly inclined from the position A, similar to the position B shown in FIG. 5. Therefore, even if the grid 48 is used in the stereographic image capturing mode, the possibility that radiation 92 will be removed by the grid 48 is small. Consequently, the solid-state detector 50 can output two radiographic images of high quality, which are free from the effect of scattered rays.

Figure 7:
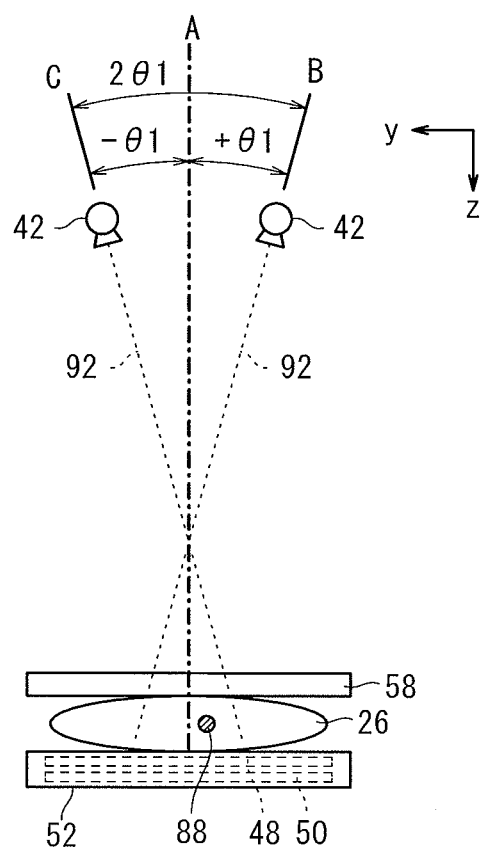
FIG. 7 is a schematic view illustrating the stereographic image capturing mode.

FIG. 7 shows an image capturing process for capturing radiographic images in the stereographic image capturing mode with the radiation source 42 placed in respective positions B, C, which are angularly spaced at respective imaging angles $+\theta1, -\theta1$ from the position A. According to this image capturing process, the solid-state detector 50 can output two radiographic images of high quality, which are free from the effect of scattered rays, similar to the image capturing processes shown in FIGS. 5 and 6.

Figure 8:
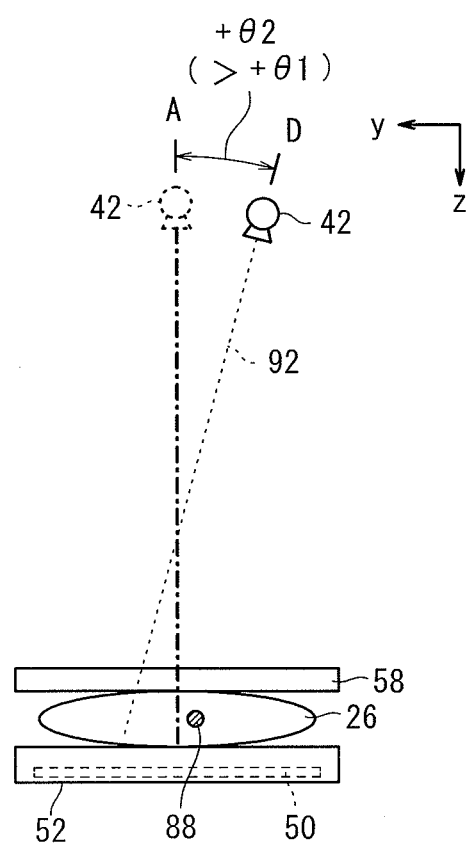
FIG. 8 is a schematic view illustrating the scout image capturing mode and the stereographic image capturing mode.

FIG. 8 shows an image capturing process for capturing a radiographic image in the scout image capturing mode (see FIG. 4) together with capturing a radiographic image in the stereographic image capturing mode with the radiation source 42 placed in a position D, which is angularly spaced at an imaging angle $+\theta2$ ($+\theta2 \leq +30°$ and $+\theta2 > +\theta1$) from the position A. At the imaging angle $+\theta2$ (position D), the radiation source 42 is inclined from the position A more greatly than in the position B (see FIG. 5). Therefore, if the grid 48 is used in the stereographic image capturing mode, radiation 92 possibly will be removed by the grid 48. Consequently, in position D, the grid 48 is not used in the stereographic image capturing mode. The solid-state detector 50 can output a radiographic image of high quality, which is free from the effect of scattered rays in the scout image capturing mode, and a radiographic image in the stereographic image capturing mode free of the grid 48. When the grid 48 is not used, the grid 48 is retracted away from the surface of the solid-state detector 50 by a moving mechanism (not shown) in the image capturing base 52.

Figure 9:
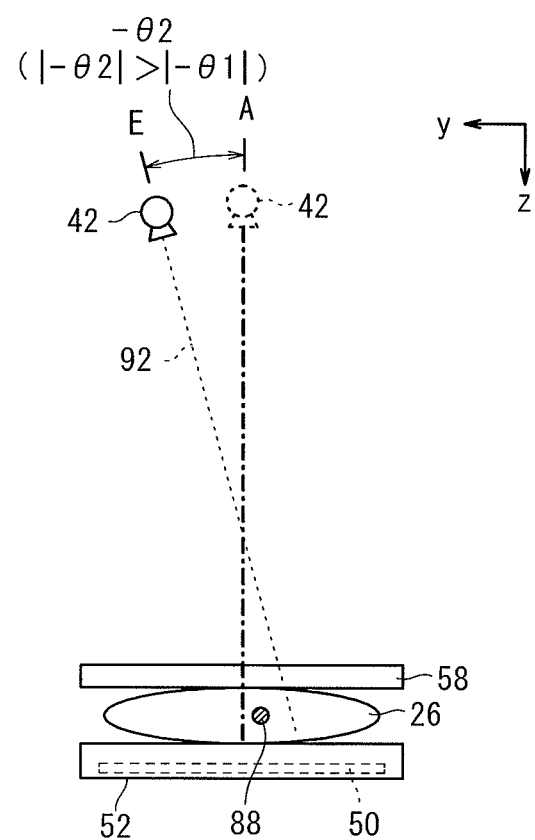
FIG. 9 is a schematic view illustrating the scout image capturing mode and the stereographic image capturing mode.

FIG. 9 shows an image capturing process for capturing a radiographic image in the scout image capturing mode together with a radiographic image in the stereographic image capturing mode with the radiation source 42 placed in a position E, which is angularly spaced at an imaging angle $-\theta2$ ($|-\theta2| \leq 30°$ and $|-\theta2| > -\theta1|$) from the position A. At the imaging angle $-\theta2$ (position E), the radiation source 42 is inclined from the position A more greatly than in the position C (see FIG. 6). Therefore, if the grid 48 is used in the stereographic image capturing mode, radiation 92 possibly will be removed by the grid 48. Consequently, in position E, the grid 48 is not used in the stereographic image capturing mode. The solid-state detector 50 can output a radiographic image of high quality, which is free from the effect of scattered rays in the scout image capturing mode, and a radiographic image in the stereographic image capturing mode free of the grid 48.

Figure 10:
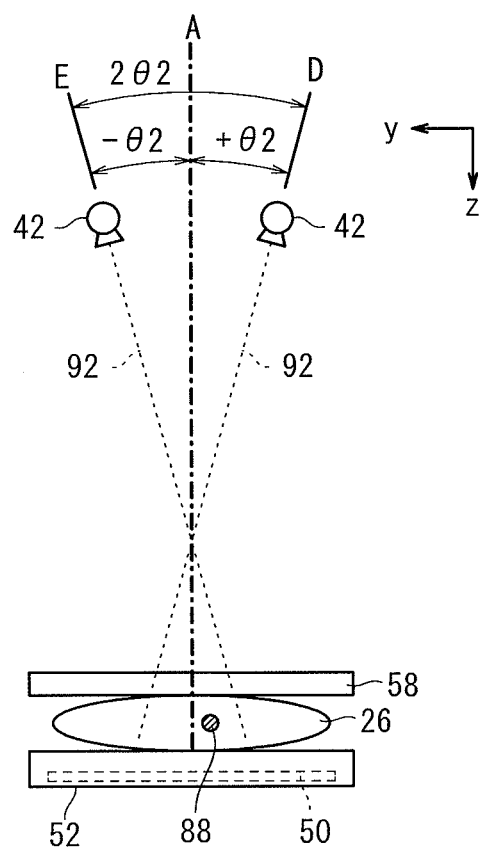
FIG. 10 is a schematic view illustrating the stereographic image capturing mode.

FIG. 10 shows an image capturing process for capturing radiographic images in the stereographic image capturing mode, with the radiation source 42 being placed respectively in positions D and E, which are angularly spaced at the respective imaging angles $+\theta2, -\theta2$ from the position A.

According to this image capturing process, the solid-state detector 50 can output two radiographic images in the stereographic image capturing mode free of the grid 48, in the same manner as the image capturing processes shown in FIGS. 8 and 9.

Figure 11:
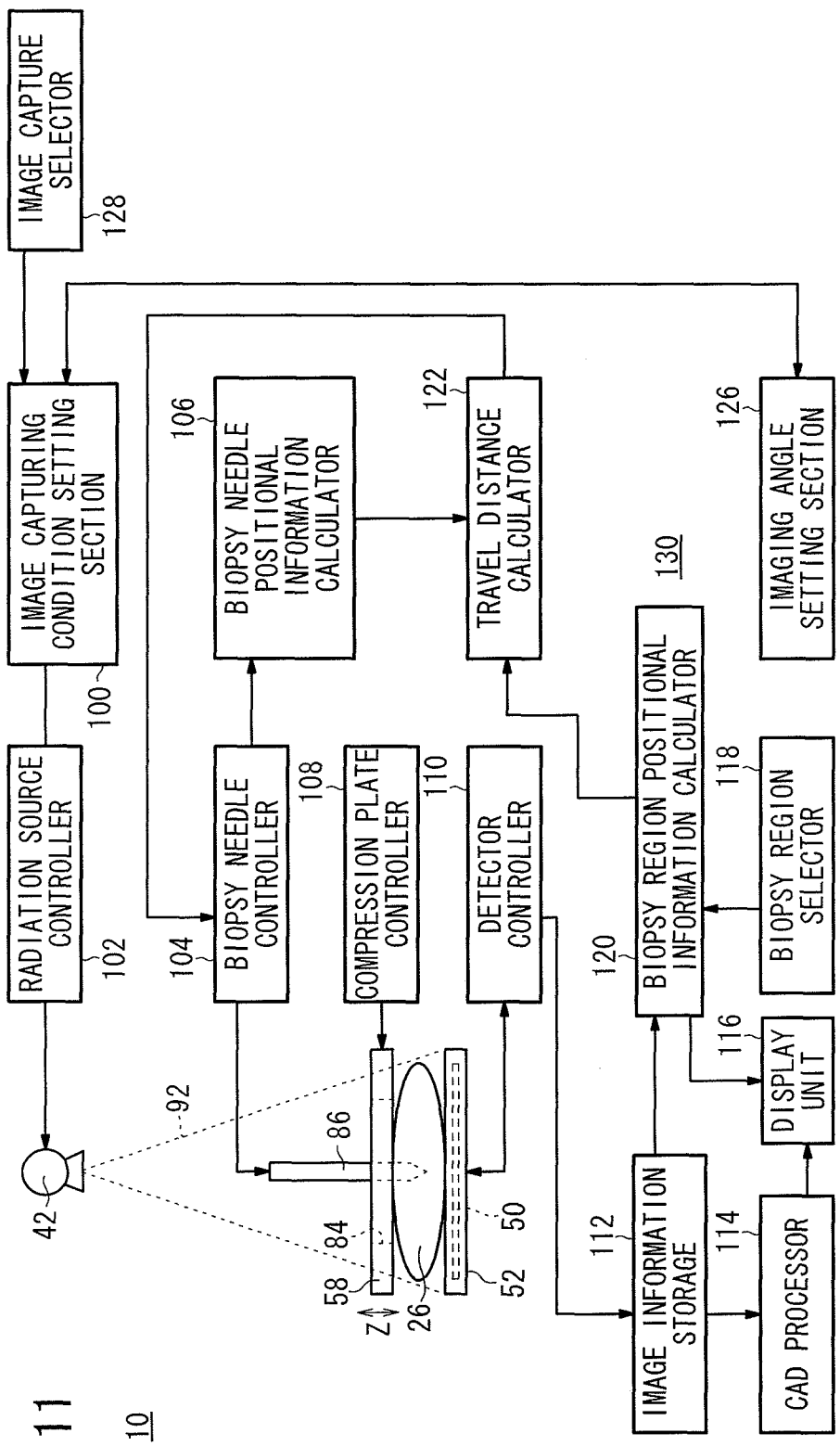
FIG. 11 is a block diagram of the biopsy apparatus shown in FIG. 1.

FIG. 11 shows in block form the biopsy apparatus 10 according to the present embodiment.

As shown in FIG. 11, the biopsy apparatus 10 includes, in addition to the mechanical components shown in FIGS. 1 through 3, a control system comprising an image capturing condition setting section 100, a radiation source controller 102, a biopsy needle controller 104, a biopsy needle positional information calculator 106, a compression plate controller 108, a detector controller 110, an image information storage 112, a CAD (Computer Aided Diagnosis) processor 114, a display unit 116, a biopsy region selector 118, a biopsy region positional information calculator 120, a travel distance calculator 122, an imaging angle setting section 126, and an image capture selector 128. The biopsy needle holding mechanism 60, the biopsy needle 86, the biopsy needle controller 104, the biopsy needle positional information calculator 106, the biopsy region selector 118, the biopsy region positional information calculator 120, and the travel distance calculator 122 collectively make up a biopsy needle positioning device 130.

The image capturing condition setting section 100 establishes image capturing conditions including tube currents, tube voltages, types of targets and filters to be used in the radiation source 42, doses of the radiation 92, irradiation times, image capturing processes (see FIGS. 4 through 10) for the scout image capturing mode and the stereographic image capturing mode, and image capturing orders. The radiation source controller 102 controls the radiation source 42 according to the image capturing conditions. The biopsy needle controller 104 controls the biopsy needle holding mechanism 60 in order to move the biopsy needle 86 to a desired position. The compression plate controller 108 moves the compression plate 58 in directions indicated by the arrow z. The detector controller 110 controls the solid-state detector 50 to convert the radiation 92 into a radiographic image, and to store the radiographic image in the image information storage 112.

The biopsy needle positional information calculator 106 calculates positional information of the tip end of the biopsy needle 86, which has been moved by the biopsy needle controller 104.

The CAD processor 114 processes the radiographic image stored in the image information storage 112. The display unit 116 displays the processed radiographic image.

If the image information storage 112 stores a single radiographic image, then the CAD processor 114 processes the radiographic image so that the radiographic image can be displayed on the display screen of the display unit 116. If the image information storage 112 stores a single radiographic image captured in the scout image capturing mode and a single radiographic image captured in the stereographic image capturing mode, then the CAD processor 114 processes the two respective radiographic images so that the two radiographic images can simultaneously be displayed on the display screen of the display unit 116. If the image information storage 112 stores two radiographic images both of which are captured in the stereographic image capturing mode, then the CAD processor 114 processes the two respective radiographic images so that the two radiographic images can simultaneously be displayed on the display screen of the display unit 116.

The display unit 116 displays a single radiographic image processed by the CAD processor 114 on the display screen, or displays two radiographic images processed by the CAD processor 114 simultaneously on the display screen.

The biopsy region selector 118 comprises a pointing device such as a mouse or the like. Using the pointing device of the biopsy region selector 118, a doctor or technician who has viewed a radiographic image or images on the display unit 116 can select a biopsy region 88 from which tissue is to be sampled, from among a plurality of biopsy regions 88 included within the displayed radiographic image. If two radiographic images are displayed on the display unit 116, then the doctor or technician selects a biopsy region 88 in one of the displayed radiographic images, and also selects a biopsy region 88 in the other displayed radiographic image, which corresponds to the biopsy region 88 in the one radiographic image.

The biopsy region positional information calculator 120 calculates the three-dimensional position of the biopsy region 88 based on the position of the biopsy region 88 in the two radiographic images, which has been selected with the biopsy region selector 118. The three-dimensional position of the biopsy region 88 may be calculated according to a known method of calculating a three-dimensional position in a stereographic image capturing mode (e.g., the method disclosed in U.S. Patent Application Publication No. 2004/0171933).

The travel distance calculator 122 calculates a distance that the biopsy needle 86 is intended to travel with respect to the biopsy region 88, based on the three-dimensional position of the biopsy region 88 as calculated by the biopsy region positional information calculator 120, and the position of the tip end of the biopsy needle 86 as calculated by the biopsy needle positional information calculator 106. The biopsy needle controller 104 moves the biopsy needle 86 based on the distance calculated by the travel distance calculator 122, so as to sample tissue from the biopsy region 88.

The imaging angle setting section 126 comprises a pointing device such as a mouse or a keyboard. The doctor or technician sets an imaging angle for the stereographic image capturing mode to a desired angle, in a range from $-\theta 1$ to $+\theta 1$ or from $-\theta 2$ to $+\theta 2$ as shown in FIGS. 4 through 10, using the pointing device or the keyboard of the imaging angle setting section 126. The imaging angle for the stereographic image capturing mode, which has been set in advance by the image capturing condition setting section 100, is changed to the imaging angle set via the imaging angle setting section 126.

The image capture selector 128 comprises a pointing device such as a mouse or a keyboard. The doctor or technician changes the imaging process, which has been set in advance by the image capturing condition setting section 100, to another imaging process using the pointing device or the keyboard of the image capture selector 128. Even after an image capturing process is performed, the doctor or technician can select a radiographic image to be used for calculating a three-dimensional position with the biopsy region positional information calculator 120, using the pointing device or the keyboard of the image capture selector 128.

The biopsy apparatus 10 according to the present embodiment basically is constructed as described above. Operation of the biopsy apparatus 10 will be described below with reference to the flowchart shown in FIG. 12.

In step S1, as shown in FIG. 12, image capturing conditions including a tube current, a tube voltage, a dose of the radiation 92, an irradiation time, an imaging angle, an image capturing process, and an image capturing order are established using the image capturing condition setting section 100 (see FIG. 11). The established image capturing conditions are set in the radiation source controller 102. Alternatively, the imaging angle setting section 126 may establish the imaging angle, and the image capture selector 128 may establish the image capturing process. Then, the technician securely positions the examinee 12 in a position lying on the top plate 22 of the bed 14, with the breast 26 hanging down through the opening 28.

In step S2, the technician positions the breast 26. More specifically, the technician places the breast 26 against the image capturing base 52 at a given position, and then the compression plate controller 108 moves the compression plate 58 toward the image capturing base 52 in the direction indicated by the arrow z, thereby compressing and positioning the breast 26.

In step S3, after the breast 26 has been positioned, the radiation source 42 is energized to capture a radiographic image of the breast 26 in the scout image capturing mode. At this time, scattered rays of radiation 92, which are produced by the breast 26, are removed by the grid 48, and radiation 92 that has passed through the breast 26 is detected by the solid-state detector 50 as representing a radiographic image. The detector controller 110 controls the solid-state detector 50 in order to acquire the radiographic image, and temporarily stores the acquired radiographic image in the image information storage 112. The CAD processor 114 processes the radiographic image stored in the image information storage 112, and displays the processed radiographic image on the display unit 116. The doctor can confirm that the breast 26, including the biopsy region 88, has been properly positioned in the captured area of the radiographic image.

Then, in step S4, the radiation source 42 is energized again in order to capture a radiographic image of the breast 26 in the stereographic image capturing mode. At this time, the stereographic image capturing mode is performed according to either one of the image capturing processes shown in FIGS. 5 through 10. According to the image capturing process shown in FIG. 5, 6, 8 or 9, a single radiographic image is captured in the stereographic image capturing mode, whereas according to the image capturing process shown in FIG. 7 or 10, two radiographic images are captured in the stereographic image capturing mode.

In step S4, if a single radiographic image is captured in the stereographic image capturing mode, then the single radiographic image is stored in the image information storage 112. In step S4, if two radiographic images are captured in the stereographic image capturing mode, then the two radiographic images are stored in the image information storage 112. Since the number of radiographic images captured according to the image capturing process shown in FIG. 5, 6, 8 or 9 is smaller than the number of radiographic images captured according to the image capturing process shown in FIG. 7 or 10, the time required to move the radiation source 42 is shorter, and hence the examination time also is shorter according to the image capturing process shown in FIG. 5, 6, 8 or 9.

The CAD processor 114 processes the two radiographic images stored in the image information storage 112, i.e., two radiographic images captured respectively in the scout image capturing mode and in the stereographic image capturing mode, or two radiographic images both of which are captured in the stereographic image capturing mode, and simultaneously displays the two processed radiographic images on the display unit 116.

In step S5, the doctor or technician who has viewed the radiographic images displayed on the display unit 116 operates the biopsy region selector 118, in order to select a desired biopsy region 88 from which tissue is to be sampled, from among a plurality of biopsy regions included within the two displayed radiographic images. The biopsy region positional information calculator 120 then calculates the three-dimensional position of the selected biopsy region 88, and displays the calculated three-dimensional position on the display unit 116.

In step S6, the doctor or technician sterilizes and gives local anesthesia to the breast 26 before piercing the breast 26 with the biopsy needle 86.

The position of the biopsy region 88 possibly may be moved as a result of local anesthesia given to the breast 26 in step S6. Therefore, the stereographic image capturing mode is performed according to one of the image capturing processes shown in FIGS. 5 through 10. The image information storage 112 then stores two radiographic images, while the CAD processor 114 processes the radiographic images stored in the image information storage 112 and displays the processed radiographic image on the display unit 116. The doctor or technician, having viewed the radiographic images displayed on the display unit 116, operates the biopsy region selector 118 and again selects a desired biopsy region from which tissue is to be sampled, from among a plurality of biopsy regions included within the two displayed radiographic images. The biopsy region positional information calculator 120 then calculates the three-dimensional position of the selected biopsy region 88, and displays the calculated three-dimensional position on the display unit 116.

In step S8, the doctor makes an incision in the surface of the breast 26 at the position where the biopsy needle 86 is intended to pierce the breast 26. Thereafter, the biopsy needle 86 is inserted into the breast 26 through the incision. The tip end of the biopsy needle 86 moves to a specified position in the breast 26 in front of the biopsy region 88.

In step S9, the stereographic image capturing mode is performed in the same manner as in step S7 in order to confirm whether the biopsy needle 86 has been inserted in alignment with the biopsy region 88 or not. The display unit 116 displays the two radiographic images produced in the stereographic image capturing mode. The doctor or technician operates the biopsy region selector 118, and again selects a desired biopsy region 88 from which tissue is to be sampled in the two displayed radiographic images. The biopsy region positional information calculator 120 then calculates the three-dimensional position of the selected biopsy region 88, displays the calculated three-dimensional position on the display unit 116, and outputs the calculated three-dimensional position to the travel distance calculator 122.

In step S10, the travel distance calculator 122 calculates the distance that the biopsy needle 86 must travel with respect to the biopsy region 88 based on the three-dimensional position of the biopsy region 88 and the position of the tip end of the biopsy needle 86, which has been calculated by the biopsy needle positional information calculator 106, and outputs the calculated distance to the biopsy needle controller 104. The biopsy needle controller 104 thus is made capable of moving the sampler 90 of the biopsy needle 86 to the biopsy region 88.

In step S11, the stereographic image capturing mode is carried out in the same manner as in steps S7 and S9 in order to confirm whether the position of the biopsy region 88 and the position and direction of the sampler 90 are in agreement with each other. At this time, the display unit 116 displays two radiographic images produced in the stereographic image capturing mode, so as to allow the doctor or technician to confirm, with ease, whether or not the position of the biopsy region 88 and the position and direction of the sampler 90 are in agreement with each other.

In step S12, the holster 80 is actuated to start drawing the biopsy region 88 and sampling tissue therefrom with the biopsy needle 86. Thereafter, the sampled tissue is examined by an examination apparatus, not shown, to determine whether the tissue is calcified or not, for example, in step S13.

In step S14, the stereographic image capturing mode is carried out in the same manner as in steps S7, S9 and S11, in order to confirm whether tissue of the biopsy region 88 has been sampled. At this time, the display unit 116 displays two radiographic images produced in the stereographic image capturing mode in order to allow the doctor or technician to confirm, with ease, whether or not the tissue of the biopsy region 88 has been sampled.

Subsequently, in step S15, the biopsy needle 86 is moved in a reverse direction, as indicated by the arrow z, and is pulled out of the breast 26, whereupon the image capturing process is ended.

If all the tissue of the biopsy region 88 has been sampled, the position of the biopsy region 88 may not need to be confirmed at a later time. Therefore, prior to step S15, in step S16, a stainless steel marker is inserted into the biopsy region 88 through the sampler 90 of the biopsy needle 86. Thereafter, in step S17, the scout image capturing mode is carried out in the same manner as in step S3 in order to confirm whether the marker has been properly inserted. At this time, the display unit 116 displays a radiographic image produced in the scout image capturing mode, so as to allow the doctor or technician to confirm, with ease, whether or not the marker has been properly inserted. Step S15 is executed after insertion of the marker has been confirmed.

According to the present embodiment, as described above, since the biopsy needle 86 is held obliquely to the radiation reception surface of the solid-state detector 50, the biopsy needle 86 is reliably prevented from overlapping the biopsy region 88 in the radiographic image produced in the scout image capturing mode. Therefore, the radiographic image produced in the scout image capturing mode can be used as a radiographic image for identifying the three-dimensional position of the biopsy region 88. In other words, the three-dimensional position of the biopsy region 88 can be identified using two radiographic images produced respectively in the scout image capturing mode and in the stereographic image capturing mode.

For identifying the position of the biopsy region 88, it heretofore has been customary to perform the scout image capturing mode, confirm that the breast 26 is included in the radiographic image produced in the scout image capturing mode, thereafter move the radiation source 42 from the imaging angle used during the scout image capturing mode, then capture a first radiographic image in the stereographic image capturing mode, move the radiation source 42 again from the imaging angle used during the stereographic image capturing mode, capture a second radiographic image in the stereographic image capturing mode, and subsequently identify the three-dimensional position of the biopsy region 88 using the two radiographic images produced in the stereographic image capturing mode. Since it takes time to move the radiation source 42 between image capturing modes, the examining time becomes prolonged and cannot be shortened.

According to the present embodiment, as described above, since the radiographic image produced in the scout image capturing mode also is used as a radiographic image for identifying the three-dimensional position of the biopsy region 88, a second radiographic image, which heretofore has been produced in the stereographic image capturing mode is no longer required. Rather, in steps S3 and S4, the three-dimensional position of the biopsy region 88 can be identified using the radiographic image produced in the scout image capturing mode and the first radiographic image produced in the stereographic image capturing mode. As a result, the number of captured radiographic images can be reduced, and hence the dose of radiation 92 applied to the breast 26 is reduced. Further, inasmuch as the number of captured radiographic images is reduced, the time required to move the radiation source 42 between image capturing modes can be shortened. Therefore, the time required to examine the biopsy region 88 is shortened, and the breast 26 is prevented from being held for a long period of time.

Furthermore, since the grid 48 is used in the scout image capturing mode, the radiographic image produced in the scout image capturing mode is of higher quality than the radiographic image produced in the stereographic image capturing mode. Accordingly, a radiographic image of high quality can be used to identify the three-dimensional position of the biopsy region 88. In other words, the three-dimensional position of the biopsy region 88 can be identified with high accuracy using the radiographic image of high quality and the first radiographic image produced in the stereographic image capturing mode.

According to the present embodiment, since two radiographic images can be produced in the stereographic image capturing mode, in addition to two radiographic images produced in the scout image capturing mode and the stereographic image capturing mode, the present embodiment can easily be applied to existing biopsy apparatus.

Even when two radiographic images are produced in the stereographic image capturing mode, since the grid 48 is used in acquiring at least one of the radiographic images with the radiation source 42 being at an imaging angle $+\theta1$ ($\leq+10°$) or at an imaging angle $-\theta1$ ($|-\theta1|\leq10°$), the three-dimensional position of the biopsy region 88 can be identified using radiographic images of high quality.

Since the three-dimensional position of the biopsy region 88 can be identified highly accurately using a radiographic image captured through use of the grid 48, a calcified region, which appears pale and vague in the radiographic images, and which represents a feature of breast cancer at an early stage, can be detected and visually recognized with ease.

Even when the radiation source 42 is at an imaging angle $+\theta2$ ($\leq+30°$) or at an imaging angle $-\theta2$ ($|-\theta2|\leq30°$), the three-dimensional position of the biopsy region 88 can reliably be identified using radiographic images produced in the stereographic image capturing mode.

With the biopsy needle 86 being held in an angular range of $0°<\varphi\leq10°$, the biopsy needle 86 is prevented from reaching the chest wall 24.

In the present embodiment, the imaging angle setting section 126 can set the imaging angle $+\theta1$, $-\theta1$, $+\theta2$, $-\theta2$ to any desired angles. The image capture selector 128 can select, in advance, two radiographic images to be produced in the scout image capturing mode and the stereographic image capturing mode, or two radiographic images to be produced in the stereographic image capturing mode. Furthermore, when the radiographic image capturing apparatus has captured a plurality of radiographic images, the image capture selector 128 can select two radiographic images produced in the scout image capturing mode and the stereographic image capturing mode, or two radiographic images produced in the stereographic image capturing mode, as the two radiographic images.

Inasmuch as the doctor or technician can set the imaging angles $+\theta1$, $-\theta1$, $+\theta2$, $-\theta2$ to any desired angles, and also can select two radiographic images to be used to identify the three-dimensional position of the biopsy region 88, the image capturing process can be selected depending on the skill of the doctor or technician, thereby resulting in a further reduction in examining time.

In the above embodiment, the examinee 12 lies on the bed 14 when tissue is sampled from the biopsy region 88. However, the principles of the present invention also can be applied to an upright biopsy apparatus, which samples a tissue in the biopsy region 88 when the examinee 12 is seated on a chair.

Although a preferred embodiment of the present invention has been shown and described in detail above, it should be understood that various changes and modifications may be made to the embodiment without departing from the scope of the invention as set forth in the appended claims.

What is claimed is:

1. A biopsy apparatus comprising:
a radiographic image capturing apparatus including a radiation source for applying radiation to a breast of a subject, a radiation detector for detecting the radiation which has passed through the breast and converting the detected radiation into a radiographic image, and a radiation source displacing mechanism for displacing the radiation source relative to the radiation detector; and
a biopsy needle positioning device including a biopsy region positional information calculator for calculating a three-dimensional position of a biopsy region of the breast based on at least two radiographic images obtained by irradiating the breast with the radiation from directions that are different from each other, a biopsy needle for piercing the biopsy region based on the calculated three-dimensional position of the biopsy region and sampling tissue of the biopsy region, and a biopsy needle holding mechanism for holding the biopsy needle, wherein the biopsy needle faces a radiation reception surface of the radiation detector, and at least in a scout image capturing mode in which the breast is irradiated with the radiation applied from the radiation source disposed on an axis perpendicular to the radiation reception surface by the radiation source displacing mechanism, the biopsy needle is held obliquely to the perpendicular axis and the radiation reception surface by the biopsy needle holding mechanism, wherein one of the at least two radiographic images comprises a radiographic image produced according to the scout image capturing mode, and wherein the other of the at least two radiographic images comprises a radiographic image produced according to the stereographic image capturing mode, in which the breast is irradiated with the radiation applied from the radiation source, which is disposed obliquely to the perpendicular axis by the radiation source displacing mechanism.

2. A biopsy apparatus according to claim 1, wherein the radiographic image capturing apparatus further includes a grid for removing scattered rays of the radiation which are produced by the breast, wherein the grid is used either in both the scout image capturing mode and the stereographic image capturing mode or in only the scout image capturing mode.

3. A biopsy apparatus according to claim 2, wherein when the grid is used in the stereographic image capturing mode, the radiation source has an imaging angle, which is equal to or smaller than 10° with respect to the axis in the stereographic image capturing mode.

4. A biopsy apparatus according to claim 1, wherein the radiation source has an imaging angle, which is equal to or smaller than 30° with respect to the axis in the stereographic image capturing mode.

5. A biopsy apparatus according to claim 4, wherein the radiographic image capturing apparatus further includes an imaging angle setting section for setting the imaging angle to an angle which is equal to or smaller than 30° with respect to the axis.

6. A biopsy apparatus according to claim 1, wherein the biopsy needle holding mechanism holds the biopsy needle at an angle equal to or smaller than 10° with respect to the axis.

7. A biopsy apparatus according to claim 1, wherein the radiographic image capturing apparatus further includes an image capture selector for selecting in advance either the two radiographic images to be produced respectively in the scout image capturing mode and the stereographic image capturing mode.

8. A biopsy apparatus according to claim 1, wherein the radiographic image capturing apparatus further includes an image capture selector for selecting, when the radiographic image capturing apparatus has captured a plurality of radiographic images, radiographic images produced respectively in the scout image capturing mode and the stereographic image capturing mode, as the two radiographic images.

9. A biopsy apparatus according to claim 1, wherein the radiographic image capturing apparatus comprises a breast image capturing apparatus further including an image capturing base for holding the breast, the image capturing base housing the radiation detector therein, and a compression plate displaceable toward the image capturing base for compressing the breast against the image capturing base; and the compression plate has an opening defined therein through which the biopsy needle can pierce the breast.

10. A biopsy apparatus according to claim 1, wherein the biopsy needle is held obliquely to a plane which the perpendicular axis passes through, and on which the radiation source is rotated on about the perpendicular axis by the radiation source displacing mechanism.

11. A biopsy apparatus according to claim 10, wherein the biopsy needle is held obliquely to the radiation reception surface and the plane in the scout image capturing mode and the stereographic image capturing mode.

12. A biopsy apparatus according to claim 1, wherein the biopsy needle is held obliquely to the perpendicular axis and the radiation reception surface at such an angle that a tip end of the biopsy needle points toward a chest wall of the subject in a plane perpendicular to the chest wall of the subject.

13. A biopsy method comprising the steps of:
detecting radiation applied from a radiation source and having passed through a breast of a subject, and converting the detected radiation into at least two radiation images with a radiation detector having a radiation reception surface, the two radiation images being produced according to a scout image capturing mode, in which the breast is irradiated with the radiation applied from the radiation source, which is disposed on an axis perpendicular to the radiation reception surface by a radiation source displacing mechanism, and a stereographic image capturing mode, in which the breast is irradiated with the radiation applied from the radiation source, which is disposed obliquely to the axis by the radiation source displacing mechanism;

calculating a three-dimensional position of a biopsy region of the breast based on the at least two radiographic images with a biopsy region positional information calculator; and piercing the biopsy region with a biopsy needle based on the calculated three-dimensional position of the biopsy region and sampling tissue of the biopsy region while the biopsy needle faces the radiation reception surface and is held obliquely to the radiation reception surface by a biopsy needle holding mechanism, wherein the biopsy needle is held obliquely to the perpendicular axis and the radiation reception surface by the biopsy needle holding mechanism at least in the scout image capturing mode.

* * * * *